(12) United States Patent
Rego et al.

(10) Patent No.: US 12,127,864 B2
(45) Date of Patent: Oct. 29, 2024

(54) MEMBRANE-BASED BREAST COMPRESSION SYSTEMS

(71) Applicant: Hologic, Inc., Marlborough, MA (US)

(72) Inventors: Alan Rego, Marlborough, MA (US); Joseph Vartolone, Marlborough, MA (US)

(73) Assignee: Hologic, Inc., Marlborough, MA (US)

( * ) Notice: Subject to any disclaimer, the term of this patent is extended or adjusted under 35 U.S.C. 154(b) by 0 days.

(21) Appl. No.: 18/196,029

(22) Filed: May 11, 2023

(65) Prior Publication Data

US 2023/0301607 A1    Sep. 28, 2023

Related U.S. Application Data

(63) Continuation of application No. 16/981,528, filed as application No. PCT/US2019/033703 on May 23, 2019, now Pat. No. 11,684,323.

(60) Provisional application No. 62/676,667, filed on May 25, 2018.

(51) Int. Cl.
| | |
|---|---|
| *A61B 6/04* | (2006.01) |
| *A61B 6/00* | (2024.01) |
| *A61B 6/02* | (2006.01) |
| *A61B 6/50* | (2024.01) |

(52) U.S. Cl.
CPC ............ *A61B 6/0414* (2013.01); *A61B 6/025* (2013.01); *A61B 6/44* (2013.01); *A61B 6/502* (2013.01)

(58) Field of Classification Search
CPC ......... A61B 6/0414; A61B 6/025; A61B 6/44; A61B 6/502
See application file for complete search history.

(56) References Cited

U.S. PATENT DOCUMENTS

| | | |
|---|---|---|
| 3,556,081 A | 1/1971 | Jones |
| 7,822,457 B2 | 10/2010 | Lokhandwalla et al. |
| 9,066,706 B2 | 6/2015 | DeFreitas et al. |
| 9,332,947 B2 | 5/2016 | DeFreitas et al. |
| 11,684,323 B2 | 6/2023 | St. Pierre |
| 2003/0167004 A1 | 9/2003 | Dines et al. |
| 2004/0109529 A1 | 6/2004 | Eberhard et al. |
| 2005/0113683 A1* | 5/2005 | Lokhandwalla ....... A61B 6/502 128/915 |

(Continued)

FOREIGN PATENT DOCUMENTS

| | | | |
|---|---|---|---|
| DE | 10 2004 017 849 | 12/2004 | |
| DE | 102004017849 A1 * | 12/2004 | ............. A61B 6/502 |

(Continued)

OTHER PUBLICATIONS

PCT International Preliminary Report on Patentability in International Application PCT/US2019/033703, mailed Dec. 10, 2020, 11 pages.

(Continued)

*Primary Examiner* — Blake C Riddick
(74) *Attorney, Agent, or Firm* — Merchant & Gould P.C.

(57) ABSTRACT

A bracket body releasably secures a compression element to the compression arm of a breast imaging system. A pair of parallel lateral arms extends from a rigid frame which extends from the bracket. A span connects the ends of the lateral arms opposite the bracket and a flexible membrane extends from the span towards the bracket body.

19 Claims, 10 Drawing Sheets

(56) References Cited

U.S. PATENT DOCUMENTS

| | | |
|---|---|---|
| 2006/0262899 A1* | 11/2006 | Al-Khalidy .......... A61B 6/0414 378/37 |
| 2007/0280412 A1 | 12/2007 | DeFreitas et al. |
| 2012/0150034 A1 | 6/2012 | DeFreitas et al. |
| 2013/0129039 A1 | 5/2013 | DeFreitas et al. |
| 2014/0044231 A1 | 2/2014 | DeFreitas et al. |
| 2014/0276068 A1 | 9/2014 | Szpak et al. |
| 2015/0282770 A1 | 10/2015 | Klanian et al. |
| 2016/0166217 A1* | 6/2016 | Davis ..................... A61B 6/025 378/208 |
| 2017/0251991 A1 | 9/2017 | Wang et al. |
| 2017/0340303 A1 | 11/2017 | Stango et al. |

FOREIGN PATENT DOCUMENTS

| | | |
|---|---|---|
| FR | 2927246 | 8/2009 |
| JP | 2016-022061 | 2/2016 |

OTHER PUBLICATIONS

PCT International Search Report and Written Opinion in International Application PCT/US2019/033703, mailed Jan. 15, 2020, 18 pages.

* cited by examiner

MEMBRANE-BASED BREAST COMPRESSION SYSTEMS

CROSS-REFERENCE TO RELATED APPLICATIONS

This application is a continuation of U.S. patent application Ser. No. 16/981,528, now U.S. Pat. No. 11,684,323, filed Sep. 16, 2020, which is a National Stage Application of PCT/US2019/033703, filed May 23, 2019, which claims priority to U.S. Provisional Patent Application No. 62/676,667, filed May 25, 2018, the disclosures of which are hereby incorporated by reference herein in their entireties. To the extent appropriate, a claim of priority is made to each of the above disclosed applications.

BACKGROUND

Compression during mammography and tomosynthesis imaging serves a number of purposes. For example, it: (1) makes the breast thinner in the direction of x-ray flux and thereby reduces patient radiation exposure from the level required to image the thicker parts of a breast that are not compressed; (2) makes the breast more uniform in thickness in the direction of x-ray flux and thereby facilitates more uniform exposure at the image plane over the entire breast image; (3) immobilizes the breast during the x-ray exposure and thereby reduces image blurring; and (4) brings breast tissues out from the chest wall into the imaging exposure field and thus allows for more tissue imaging. As the breast is being compressed, typically a technician manipulates the breast to position it appropriately and counter the tendency that compression has of pushing breast tissue toward the chest wall and out of the image field.

Standard compression methods for mammography and tomosynthesis use a movable, rigid, radiolucent compression paddle. The breast is placed on a breast support platform that typically is flat, and the paddle then compresses the breast, usually while a technician or other health professional is holding the breast in place. The technician may also manipulate the breast to ensure proper tissue coverage in the image receptor's field of view.

One known challenge in mammography and breast tomosynthesis is the discomfort the patient may feel when the breast is compressed, which must be done with sufficient force to immobilize the breast and spread out the breast tissues for x-ray imaging. Discomfort may potentially cause the patient to move, which negatively impacts image quality. Discomfort may also potentially dissuade patients from getting screened for breast cancer. Another known challenge is to ensure that the imaged field includes the desired amount of breast tissue.

SUMMARY

In one aspect, the technology relates to a compression element for a breast imaging system, the compression element having: a bracket body for releasably securing the compression element to a compression arm of the breast imaging system; a rigid frame extending from the bracket, wherein the rigid frame includes: a first lateral arm extending from the bracket body; a second lateral arm extending from the bracket body substantially parallel to the first lateral arm; and a span connecting the first lateral arm and the second lateral arm, wherein the span connects ends of the first lateral arm and the second lateral arm at a location opposite the bracket; and a flexible membrane extending from the span towards the bracket body. In an example, the flexible membrane is overmolded onto at least a portion of the span. In another example, the flexible membrane is overmolded onto a portion of at least one of the first lateral arm, the second lateral arm, and the bracket body. In yet another example, the compression element further includes a position adjustment mechanism secured to the bracket body, wherein a portion of the flexible membrane disposed opposite the span is secured to the position adjustment mechanism. In still another example, the position adjustment mechanism includes: a housing secured to the bracket body; an actuator disposed within the housing; and a rod engaged with the actuator, wherein the rod includes an interior portion disposed within the housing and exterior portion disposed outside of the housing, and wherein the flexible membrane is secured to the exterior portion.

In another example of the above aspect, the actuator is configured to adjust a position of the rod relative to the bracket body. In an example, the bracket body has a pivoting bracket for releasably securing the compression element to the compression arm.

In another aspect, the technology relates to a compression element for a breast imaging system, the compression element having: a rigid unitary frame having: a bracket body having a bracket connection; a first lateral arm extending from a first end of the bracket body; a second lateral arm extending from a second end of the bracket body; a span extending between the first lateral arm and the second lateral arm, wherein the span includes a profile having a substantially vertical major axis; and a flexible membrane spanning the rigid unitary frame. In an example, the rigid unitary frame includes smooth curved corners at each end of the bracket body, the first lateral arm, the second lateral arm, and the span. In another example, the flexible membrane is overmolded over at least a portion of the rigid unitary frame. In yet another example, the bracket connection includes a post extending from the bracket body. In still another example, the bracket connection has a rotatable connector.

In another aspect, the technology relates to a breast imaging system having: a gantry; a compression system pivotably connected to the gantry about a compression system axis, wherein the compression system includes: a support platform having a platform axis extending substantially parallel to the compression system axis, wherein the support platform is substantially curved about the platform axis; a compression element movably disposed along an axis substantially parallel to the platform axis; an x-ray receptor disposed within the support platform; and a tube head including an x-ray source pivotably coupled to the gantry for pivotable movement independent of a movement of the compression system. In an example, the compression element includes a flexible membrane. In another example, the compression element further includes a pair of arms extending from a bracket releasably connected to the compression system, wherein the flexible membrane spans the pair of arms. In yet another example, the flexible membrane includes a plurality of flexible membranes. In still another example, each arm of the pair of arms has a flexure sensor.

In another example of the above aspect, at least one arm of the pair of arms has a rotatable sheath secured to the flexible membrane for varying a tension of the flexible membrane between the pair of arms. In an example, at least one arm of the pair of arms includes a plurality of rotatable sheaths, each of the rotatable sheaths secured to one of the plurality of flexible membranes, and wherein each of the plurality of rotatable sheaths is configured to vary a tension of the associated flexible membrane. In another example, at least one arm of the pair of arms is laterally translatable for varying a tension of the flexible membrane between the pair of arms.

DETAILED DESCRIPTION

Figure 1A:
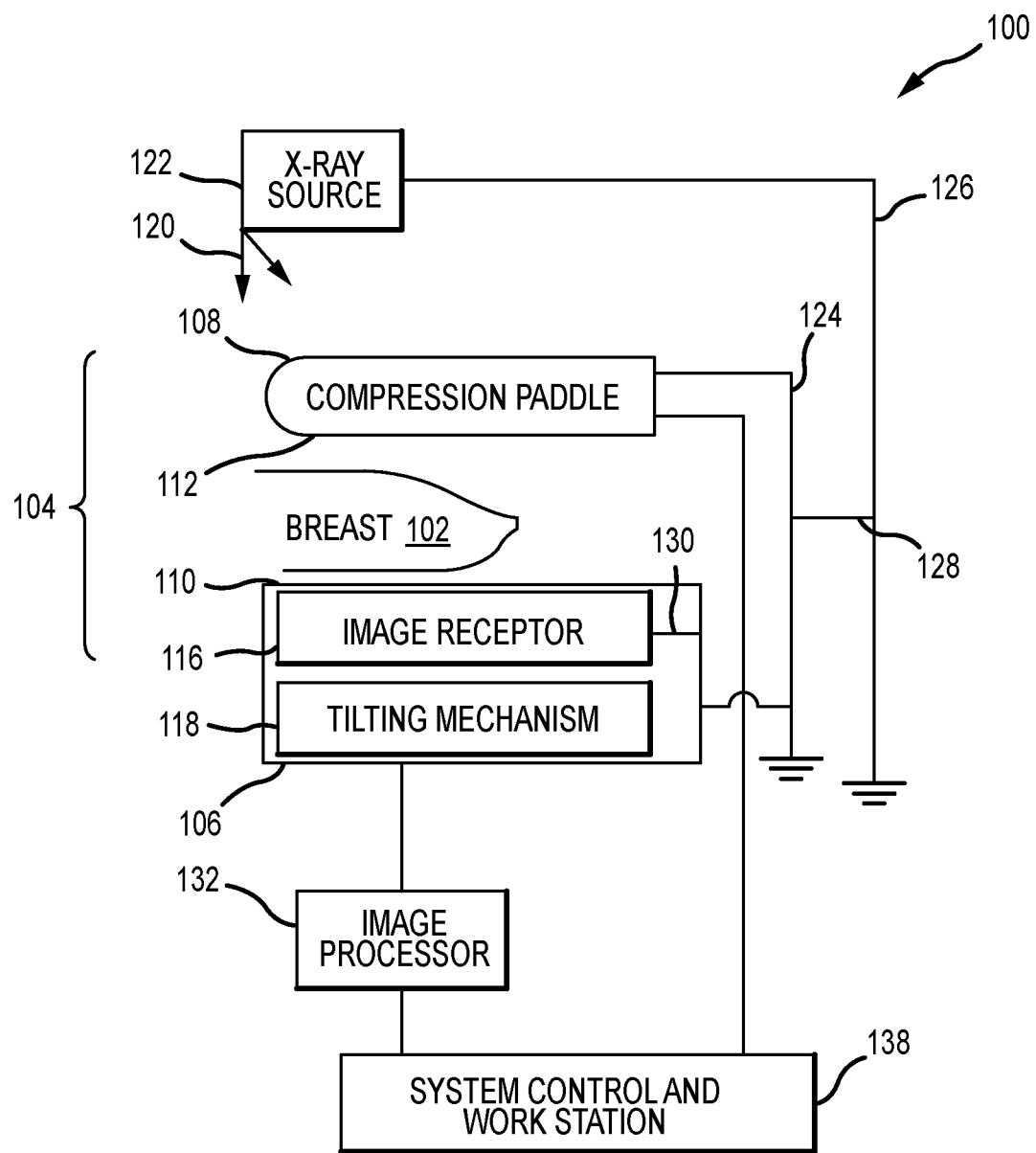
FIG. 1A is a schematic view of an exemplary imaging system.
Figure 1B:
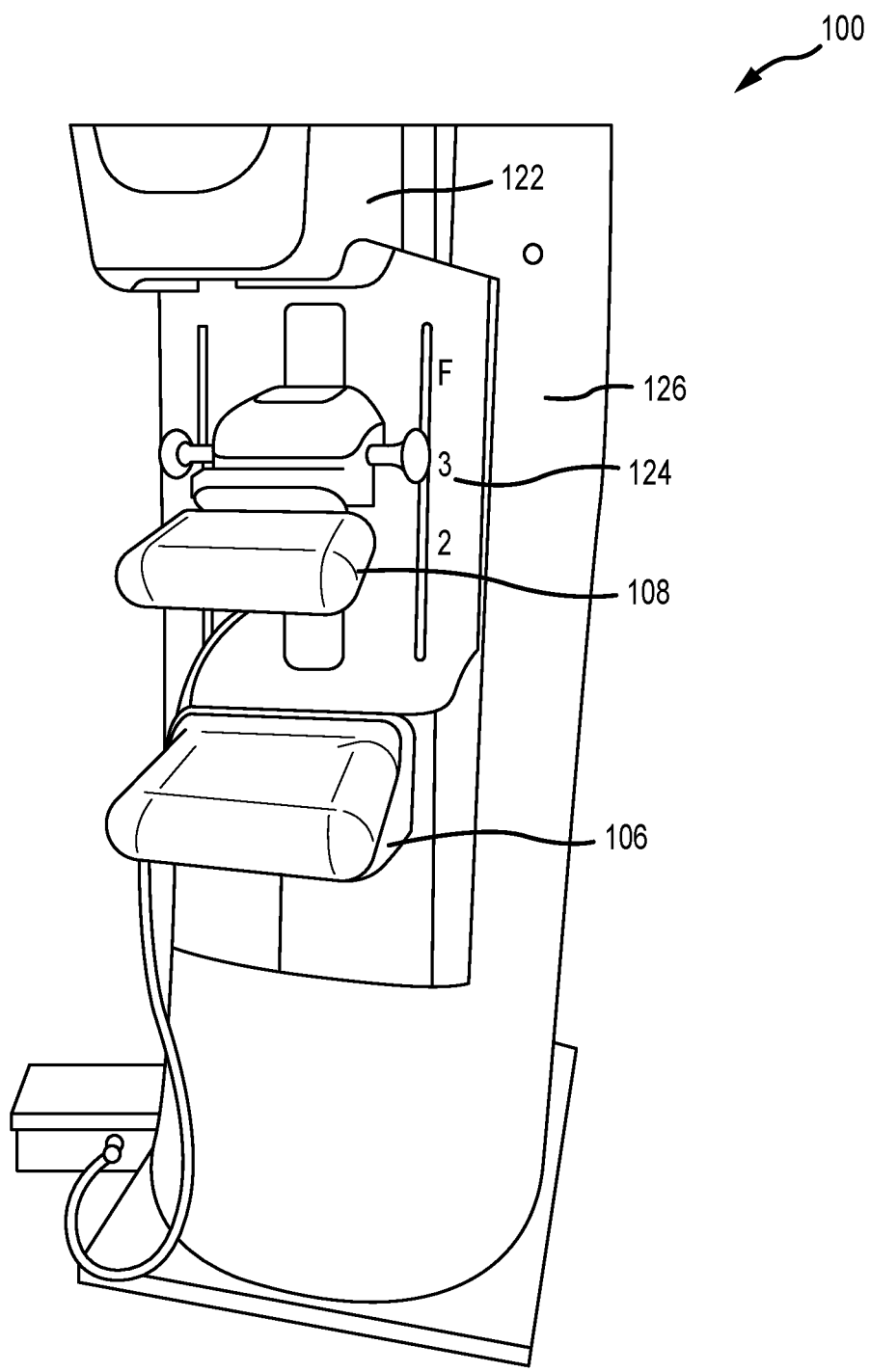
FIG. 1B is a perspective view of the imaging system of FIG. 1A.

FIG. 1A is a schematic view of an exemplary imaging system 100. FIG. 1B is a perspective view of the imaging system 100. Referring concurrently to FIGS. 1A and 1B, the imaging system 100 immobilizes a patient's breast 102 for x-ray imaging (either or both of mammography and tomosynthesis) via a breast compression immobilizer unit or compression system 104 that includes a static breast support platform 106 and a moveable compression paddle 108. The breast support platform 106 and the compression paddle 108 each have a compression surface 110 and 112, respectively, that move towards each other to compress and immobilize the breast 102. In known systems, the compression surface 110, 112 is exposed so as to directly contact the breast 102. The platform 106 also houses an image receptor 116 and, optionally, a tilting mechanism 118. The immobilizer unit 104 is in a path of an imaging beam 120 emanating from x-ray source 122, such that the beam 120 impinges on the image receptor 116.

The compression system 104 is supported on a first support arm 124 and the x-ray source 122 is supported on a second support arm, also referred to as a tube arm 126. For mammography, support arms 124 and 126 can rotate as a unit about an axis 128 between different imaging orientations such as cranial-caudal (CC) and mediolateral oblique (MLO) views, so that the system 100 can take a mammogram projection image at each orientation. In operation, the image receptor 116 remains in place relative to the platform 106 while an image is taken. The immobilizer unit 104 releases the breast 102 for movement of arms 124, 126 to a different imaging orientation. For tomosynthesis, the support arm 124 stays in place, with the breast 102 immobilized and remaining in place, while at least the tube arm 126 rotates the x-ray source 122 relative to the immobilizer unit 104 and the compressed breast 102 about the axis 128. The system 100 takes plural tomosynthesis projection images of the breast 102 at respective angles of the beam 120 relative to the breast 102. As such, the compression system 104 and tube arm 126 may be rotated discrete from each other, unless matched rotation is required or desired for an imaging procedure.

Concurrently and optionally, the image receptor 116 may be tilted relative to the breast support platform 106 and in sync with the rotation of the second support arm 126. The tilting can be through the same angle as the rotation of the x-ray source 122, but may also be through a different angle selected such that the beam 120 remains substantially in the same position on the image receptor 116 for each of the plural images. The tilting can be about an axis 130, which can but need not be in the image plane of the image receptor 116. The tilting mechanism 118 that is coupled to the image receptor 116 can drive the image receptor 116 in a tilting motion. For tomosynthesis imaging and/or CT imaging, the breast support platform 106 can be horizontal or can be at an angle to the horizontal, e.g., at an orientation similar to that for conventional MLO imaging in mammography. The system 100 can be solely a mammography system, a CT system, or solely a tomosynthesis system, or a "combo" system that can perform multiple forms of imaging. An example of such a combo system is been offered by the assignee hereof under the trade name Selenia Dimensions.

When the system is operated, the image receptor 116 produces imaging information in response to illumination by the imaging beam 120, and supplies it to an image processor 132 for processing and generating breast x-ray images. A system control and work station unit 138 including software controls the operation of the system and interacts with the operator to receive commands and deliver information including processed-ray images.

One challenge with the imaging system 100 is how to immobilize and compress the breast 102 for the desired or required imaging. A health professional, typically an x-ray technician, generally adjusts the breast 102 within the immobilizer unit 104 while pulling tissue towards imaging area and moving the compression paddle 108 toward the breast support platform 106 to immobilize the breast 102 and keep it in place, with as much of the breast tissue as practicable being between the compression surfaces 110, 112.

The technologies described herein relate to a breast compression and imaging system that utilize flexible compression element, e.g., manufactured of a translucent or transparent membrane, which may be elastic or otherwise flexible, in lieu of a rigid compression paddle. A flexible membrane compression element displays a number of features unavailable with prior art compression systems. For example, a flexible membrane compression element cannot apply as high of a compressive force to the breast. Thus, the flexible compression element may stabilize the breast for imaging without causing the discomfort typically associated with a rigid paddle. This can both improve the imaging experience itself for the patient, as well improve even the perception of the experience, which may result in fewer patients avoiding breast imaging procedures entirely. Flexible membranes, unlike some other cushioning elements utilized with rigid paddles, may be transparent, or at least translucent, which may aid a technician in positioning a breast. Further, use of membranes for compression may limit attenuation present with other cushioning materials. Flexible membranes may also be tensioned or released during compression and imaging procedures, thereby increasing patient comfort.

Figure 2:
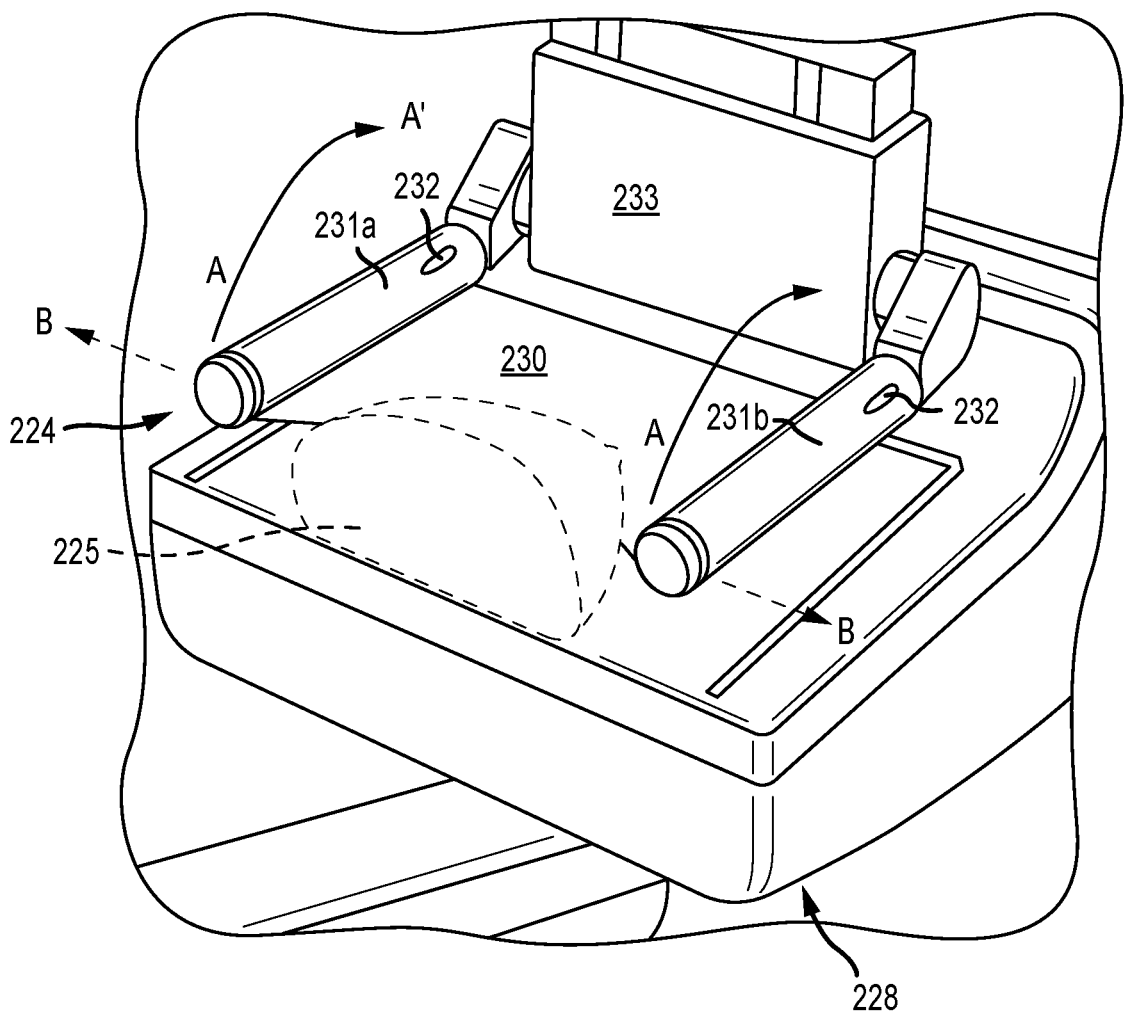
FIG. 2 depicts a partial perspective view of an imaging system utilizing an example of a flexible compression element.

FIG. 2 illustrates a flexible membrane compression element 224 that includes a material 230, positioned between a pair of opposing arms 231a and 231b, wherein each of the arms are attached to a base 233, which may be raised and lowered as described herein. The material 230 is sufficiently sheer so as to be transparent to x-rays, with minimal to no attenuation of x-rays. In one embodiment, the material 230 is formed from a porous fabric, for example a polyester or nylon blend fabric, such as tulle or the like. The material 230 may be inelastic, or may be formed of a material with a limited amount of elasticity. In other examples, the material 230 may be impermeable to liquid, and may be flexible or otherwise compliant, and may be of sufficient tensile strength and elasticity to immobilize a breast during compression and imaging.

In examples, the material may disposable. Various methods of providing a disposable positioning paddle are within the scope of the present disclosure. Examples include arranging the material on a two-sided frame having mating edge, wherein the mating edges are slid into mating slots of each of the arms 231a and 231b. Disposable compression elements may be provided in dispenser that may be accessed by a technologist between patients. Alternatively, a disposable or re-usable immobilization paddle may be provided which includes the material as part of the paddle. A switch, dial or other mechanism may be provided on the arms or base of the paddle to increase the "tightness" of the material. The tightness may be adjusted after the material is positioned over the patient's breast, before the material is placed on the patient's breast, or a combination of both before and after. Tightness can be adjusted manually by a technologist (either on the gantry or otherwise), adjusted until patient provides feedback to stop, or automatically by the system, in accordance with designed stabilization/compression force and through computer logic.

In another example, a mesh screen may be slid into the receptacles within the arm, a dial or other control may provide a first adjustment to the tightness of the screen, the paddle may be moved vertically downward into contact with the breast, and subsequent adjustment to the screen may be used to achieve final immobilization. Alternatively, the mesh material may simply be brought into contact with the breast to a desired compression, as typically done for mammography screening. In still a further embodiment, the arms 231a, 231b, may be coupled to the base 233 of the paddle to permit their movement along the path generally represented by the arrows A in FIG. 2. The immobilization arm of the gantry may be brought down towards the patient's breast with the arms in position A'. When the immobilization arm has reached the desired orientation relative to the patient's breast, the arms may then be brought down into the position shown in FIG. 2, securing the material over the patient's breast and allowing for any tightening that is desired to be performed.

In another example, the arms 231a and 231b are also adjustable along the x-axis, as shown in the arrows B in FIG. 2. Adjustment of the arms in this manner may allow for increased tension to be applied to the breast in the chest area of the patient, while less tension is applied to the nipple, as is sometimes desired for improved tissue capture. Components that detect flexure of the lateral arms 231a, 231b, such as strain gauges 232 or other elements may also be utilized. These strain gauges 232 may send a signal to a processor or controller associated with the flexible membrane compression element 224, which may be used to determine, for example, an approximate thickness of the compressed breast. The accuracy of this approximation will increase if the properties (area, elastic modulus, etc.) of the flexible material 230 are known. Additional examples of flexible membrane compression elements, displaying additional features and functionality, are described herein.

Figure 3:
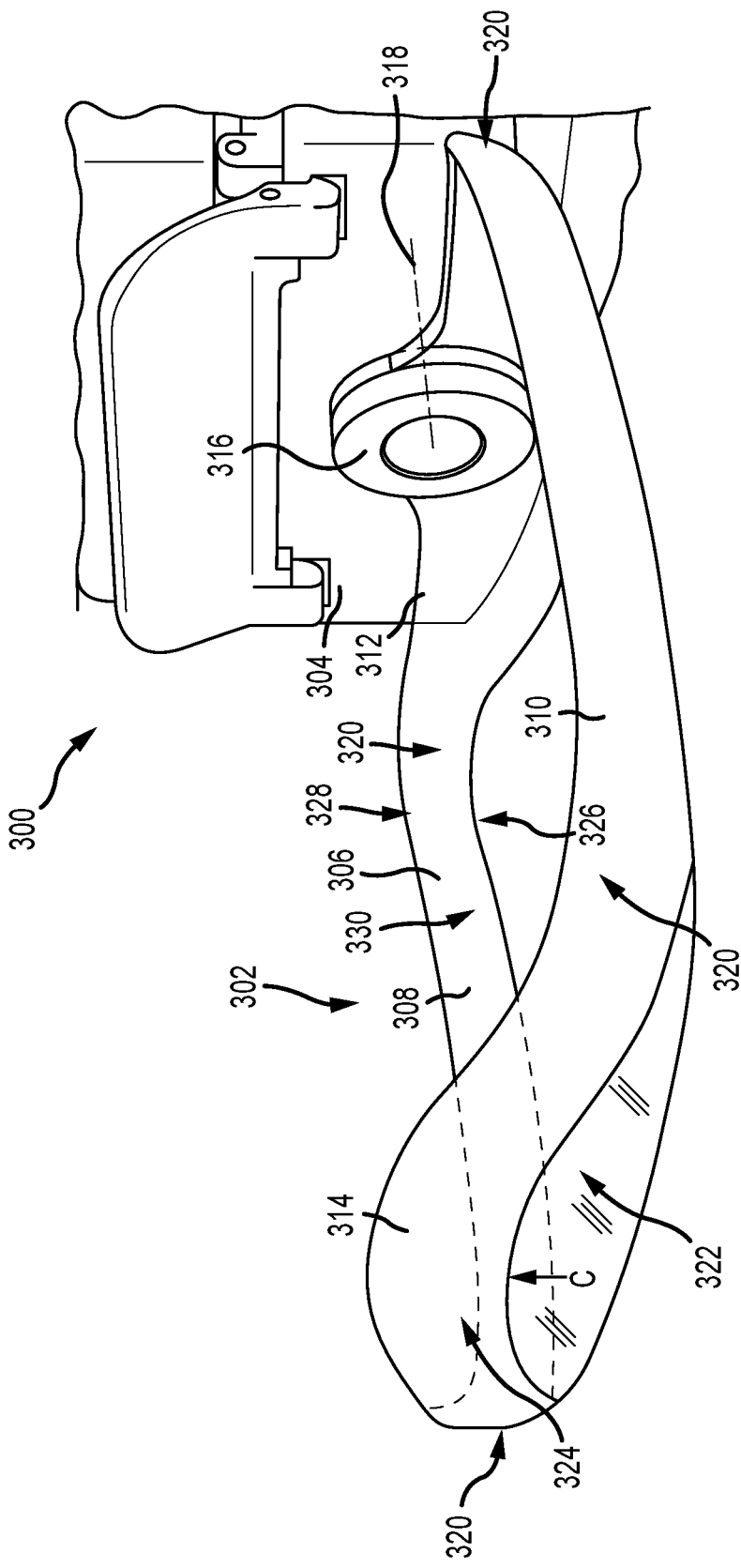
FIG. 3 depicts a partial perspective view of an imaging system utilizing another example of a flexible compression element.

FIG. 3 depicts a partial perspective view of an imaging system 300 utilizing another example of a flexible compression element 302. The flexible compression element 302 is removably secured to a compression arm 304 of the imaging system 300. The compression element 302 includes a rigid unitary frame 306 that forms a complete perimeter thereof. The unitary frame 306 may be a clear or translucent plastic such as Ixef™ PARA (polyarylamide) 50% glass-filled nylon, available from Solvay Group, Belgium. The unitary frame 306 includes a first lateral arm 308 and a second lateral arm 310 that extend from opposite ends of a bracket body 312. A span 314 is opposite the bracket body 312 and connects the two lateral arms 308, 310. A bracket connection 316 pivotably connects the compression element 302 to the compression arm 304. The bracket connection 316 includes a post 318 extending from the bracket body 312. This post 318 may be inserted into a corresponding receiver (not shown) in the compression arm 304 so as to pivotably P connect the compression element 302 to the compression arm 304. A spring, such as a torsion spring, or an elastomer spring element may be used to maintain the compression element 302 in a generally level orientation, relative to the horizon, but still allow for pivotal movement during use.

The various arms 308, 310, bracket body 312, and span 314 each include a thin profile having generally smooth curvatures. The corners 320 at each interface between ends of these elements 308, 310, 312, 314 are generally curved so as to reduce uncomfortable pinch points on the compression element 302. The thin profile of each of elements 308, 310, 312, 314 has a major axis and a minor axis. In generally, the major axis may correspond to the longest width dimension of the element, while the minor axis may correspond to a thin width dimension of the element, generally centrally located within the element. Although the elements 308, 310, 312, 314 may be oriented in any configuration, it is generally advantageous to orient the span 314 such that the major axis of the profile is substantially vertical, as depicted, for several reasons. This allows the span 314 to be placed tight to the chest wall of a patient, without projecting too far therefrom. Any artifacts potentially formed by the span 314 to be minimized in that the narrowest dimensions of the span are generally parallel to the emitted x-rays. As the compression element 302 is pressed downward against the breast, the vertical major axis allows the span to better resist deformation forces there against. Further, an upward curvature C of the span 314 from the first and second lateral arms 308, 310 allows the force from a membrane 322 to be applied to the breast proximate the chest wall, which may be more comfortable.

The membrane 322 is configured to span or be stretched between all of the elements 308, 310, 312, 314, including the corners 320. Various materials may be utilized for the membrane, including naturally-occurring rubbers, plastics, films, displaying varying degrees of flexibility, elasticity, and tension may be utilized. Some examples include thermoplastic polyurethanes such as Pellethane™ TPU, from Lubrizol LifeSciences, and having a 95 Shore A durometer. Various connection configurations of the membrane 322 to the frame 306 are contemplated. The membrane may be secured to an outer surface 324 of the frame, either with an appropriate adhesive or via heat welding. The membrane 322 may be secured to or proximate a lower edge 326 or an upper edge 328 of the frame 306. In the latter case, it may be desirable to wrap the membrane about the outer surface 324, so as to maintain tension thereon during compression procedures. In another example, the membrane 322 may be overmolded onto the frame 306 so as to surround the outer surface 324, an inner surface 330, and both upper 328 and lower 326 edges. This overmolding may be particularly desirable to form a robust connection to the frame 306 while eliminating the potential for creases in the membrane, points of localized stress, and so forth.

Figure 4A:
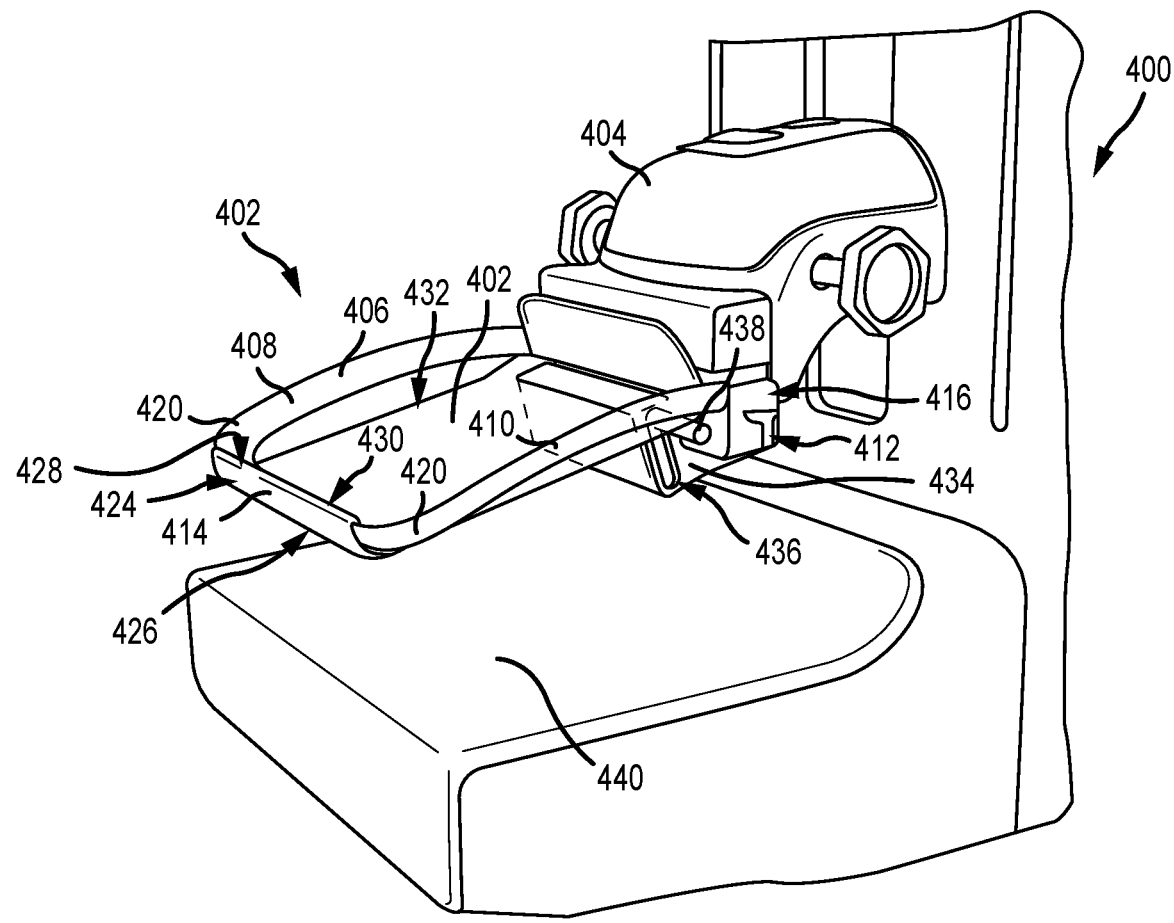
FIGS. 4A and 4B depict partial perspective views of an imaging system utilizing another example of a flexible compression element, with the flexible compression element depicted in a first position and a second position, respectively.
Figure 4B:
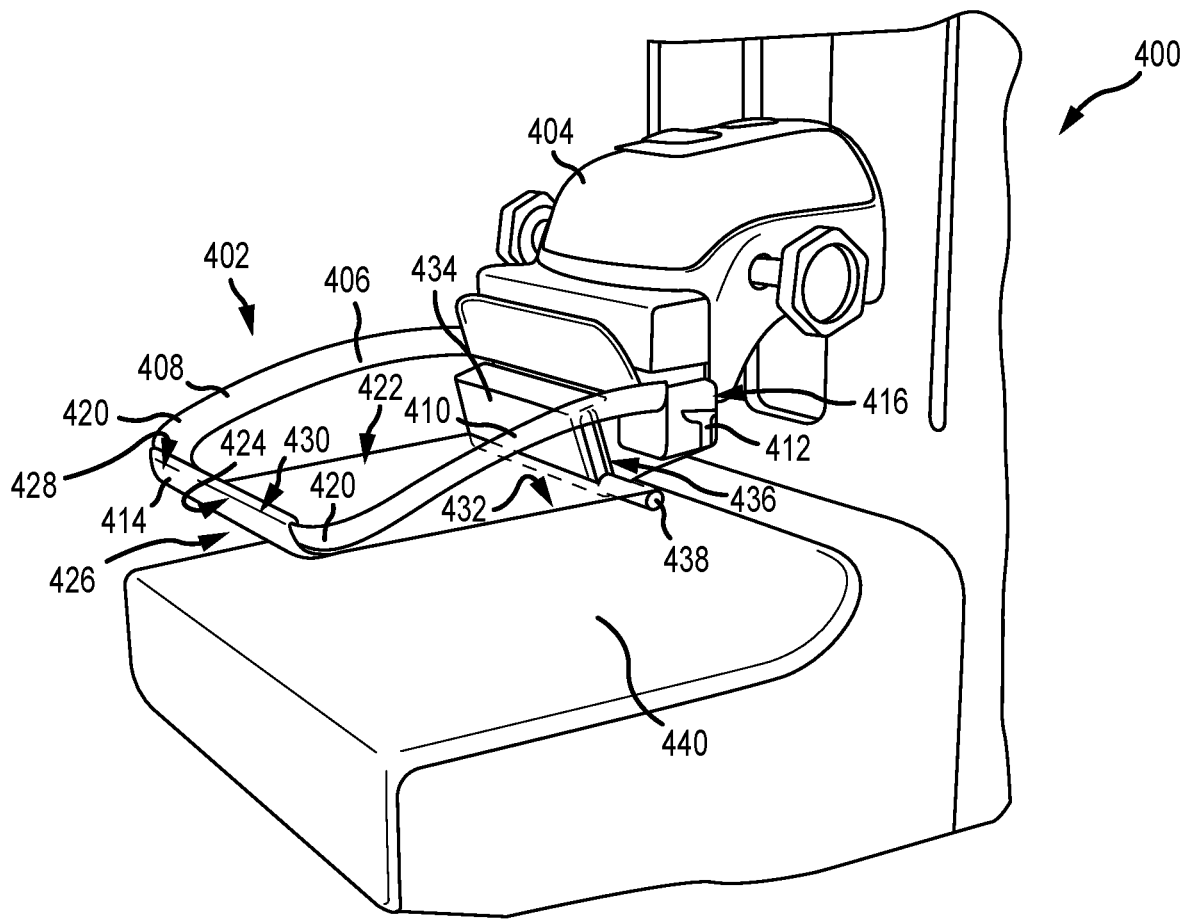

FIGS. 4A and 4B depict partial perspective views of an imaging system 400 utilizing another example of a flexible compression element 402, with the flexible compression element 402 depicted in a first position (FIG. 4A) and a second position (FIG. 4B), respectively. The flexible compression element 402 is removably secured to a compression arm 404 of the imaging system 400. The compression element 402 includes a generally U-shaped frame 406 having a first lateral arm 408, a second lateral arm 410, and a span 414 connecting the arms 408, 410. The frame 406 is connected at ends of the arms 408, 410 to a bracket body 412, which is ultimately removably connected to the compression arm 404. Any configuration of different bracket connections (not shown) may be utilized to secure the bracket body 412 to the compression arm 404. Such known configurations include pivoting connections, tilting connections, or even connections that enable lateral movement of the compression element 402 relative to the compression arm. Such connections are described, for example, in U.S. Pat. Nos. 9,066,706 and 9,332,947; as well as U.S. Patent Application Publication No. 2017/0340303, the disclosure of which are hereby incorporated by reference herein in their entireties.

Similar to the example depicted in FIG. 3, above, the various arms 408, 410 and span 414 each include a thin profile having generally smooth curvatures. The corners 420 between ends of these elements 408, 410, 414 are generally curved so as to reduce uncomfortable pinch points on the compression element 402. The thin profile of each of elements 408, 410, 414 may again be oriented in any configuration, though it may be desirable to orient the span 414 such that a major axis thereof is substantially vertical, for reasons described above. The membrane 422 may be secured, via adhesive, heat welding, or overmolding, to the span 414. The membrane 422 may be secured to or proximate a lower edge 426 or an upper edge 428, or secured to an outer surface 424 or an inner surface 430, or overmolded entirely onto the span 414. Lateral edges 432 of the membrane 422 are not secured to the frame 406 so as to enable the functionality further described below.

The bracket body 412, in this case, includes a housing 434 defining a slot 436 on either side thereof. A rod 438 extends from both slots 436 and the membrane 422 may be secured thereto, using any of the securement techniques described herein. The rod 438 is connected to a mechanism within the housing 434 that moves the rod up or down. An upper position of the rod is depicted in FIG. 4A, while a lower position is depicted in FIG. 4B. By moving the rod 438 between these two positions, the membrane 422 may be moved so as to apply force along an upper area of the breast. When in the upper position of FIG. 4A, the membrane 422 is disposed at an angle to the breast support platform 440 of the imaging system 400, while in the lower position of FIG. 4B, the membrane 422 is disposed substantially parallel to the support platform 440. Depending on the length, size, or configuration of the housing 434 or slot 436 (or of the rod(s) 438 extending therefrom), configurations where the rod end of the membrane 422 may be brought closer to the support platform 440 than the position of the span 414 are also possible.

Figure 5:
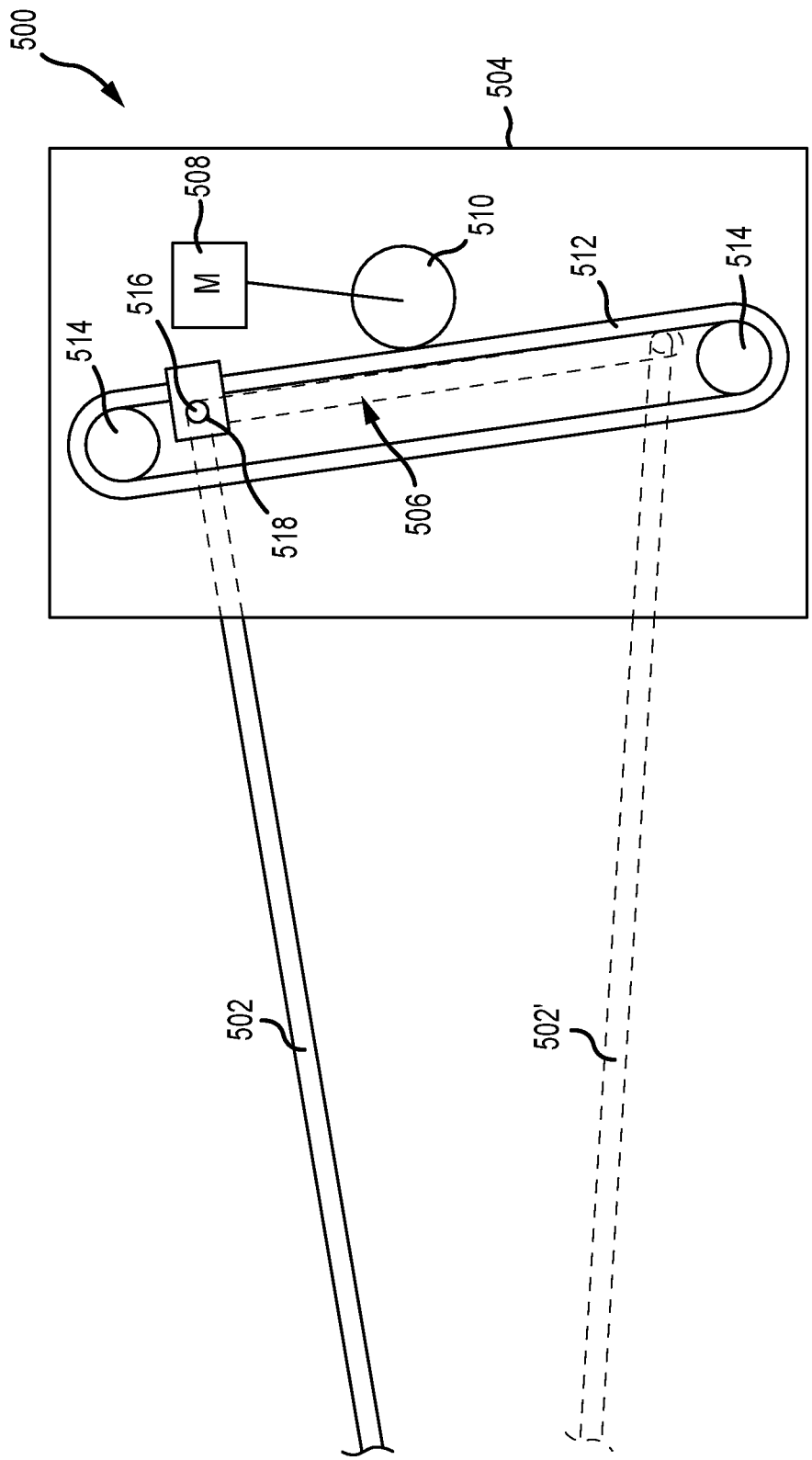
FIG. 5 depicts a schematic view of a position adjustment mechanism of a breast compression element utilized in an imaging system.

FIG. 5 depicts a schematic view of a position adjustment mechanism 500 of a breast compression element having a membrane 502 utilized in an imaging system. The mechanism 500 is disposed within a housing 504 that in certain cases forms part of the bracket body 506, as described herein. A slot 506 in the housing 504 is depicted. The position adjustment mechanism 500, in this example, is configured as a cable drive mechanism including a motor or actuator 508. The motor or actuator 508 rotates a drive pulley 510 that is engaged with a cable or belt 512. The cable 512 is routed around two tensioning rollers 514 disposed proximate either end of the slot 506. A rod 516 projects from the slot 516 to an exterior of the housing and includes, interior to the housing 504, a follower 518 engaged with the cable 512. As described above, a portion of the rod 516 exterior to the housing is secured to the membrane 502. As the cable 512 is actuated, the follower 518 moves along the cable 512, thus changing a position of the rod 516 and, subsequently, position of the compression membrane 502. The position of the membrane when the rod 516 has moved to the opposite end of the slot 516 is depicted as 502'.

Figure 6A:
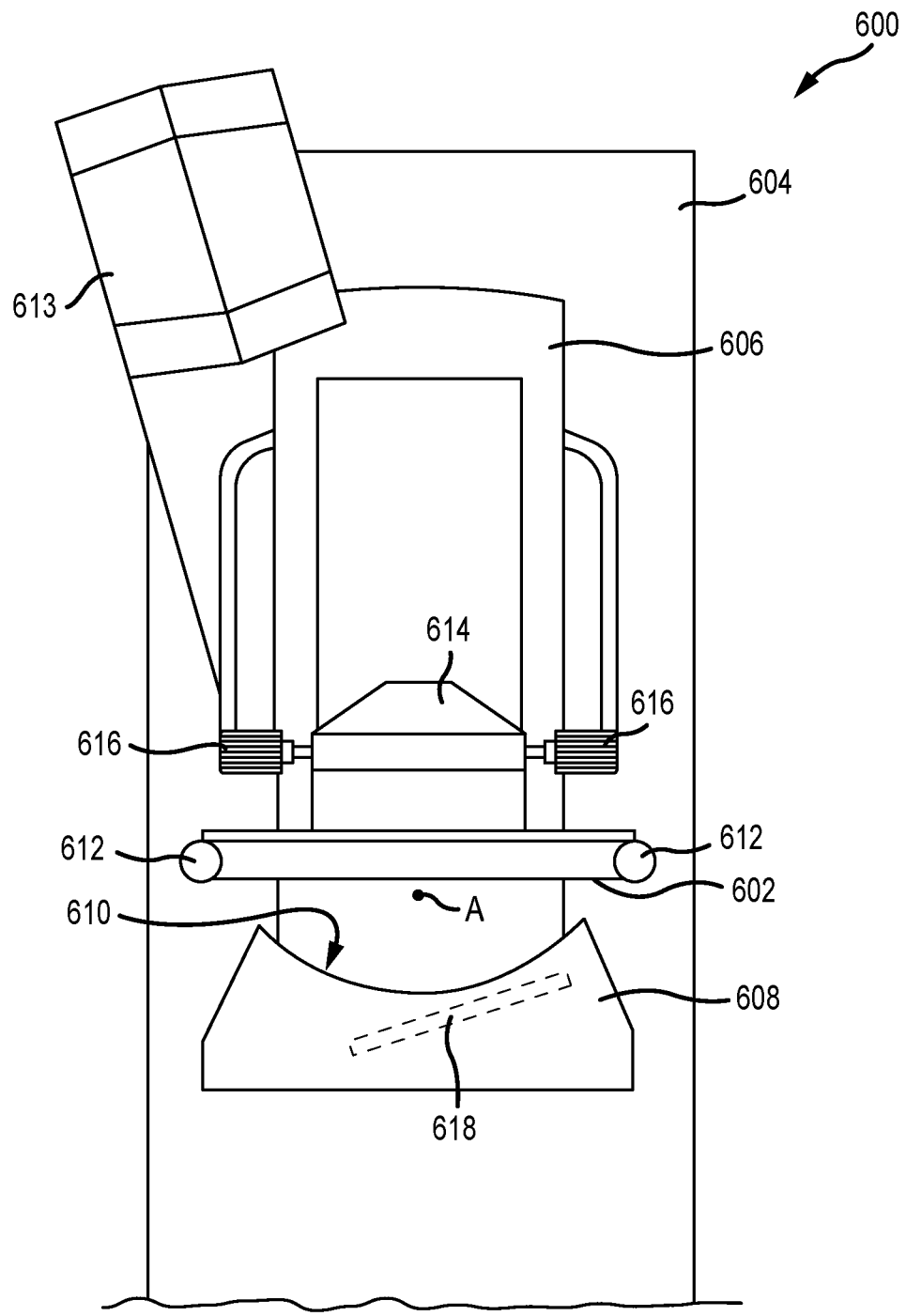
FIGS. 6A and 6B depict a partial front view of another example of an imaging system utilizing a flexible compression element, with the flexible compression element depicted in a first position and a second position, respectively.
Figure 6B:
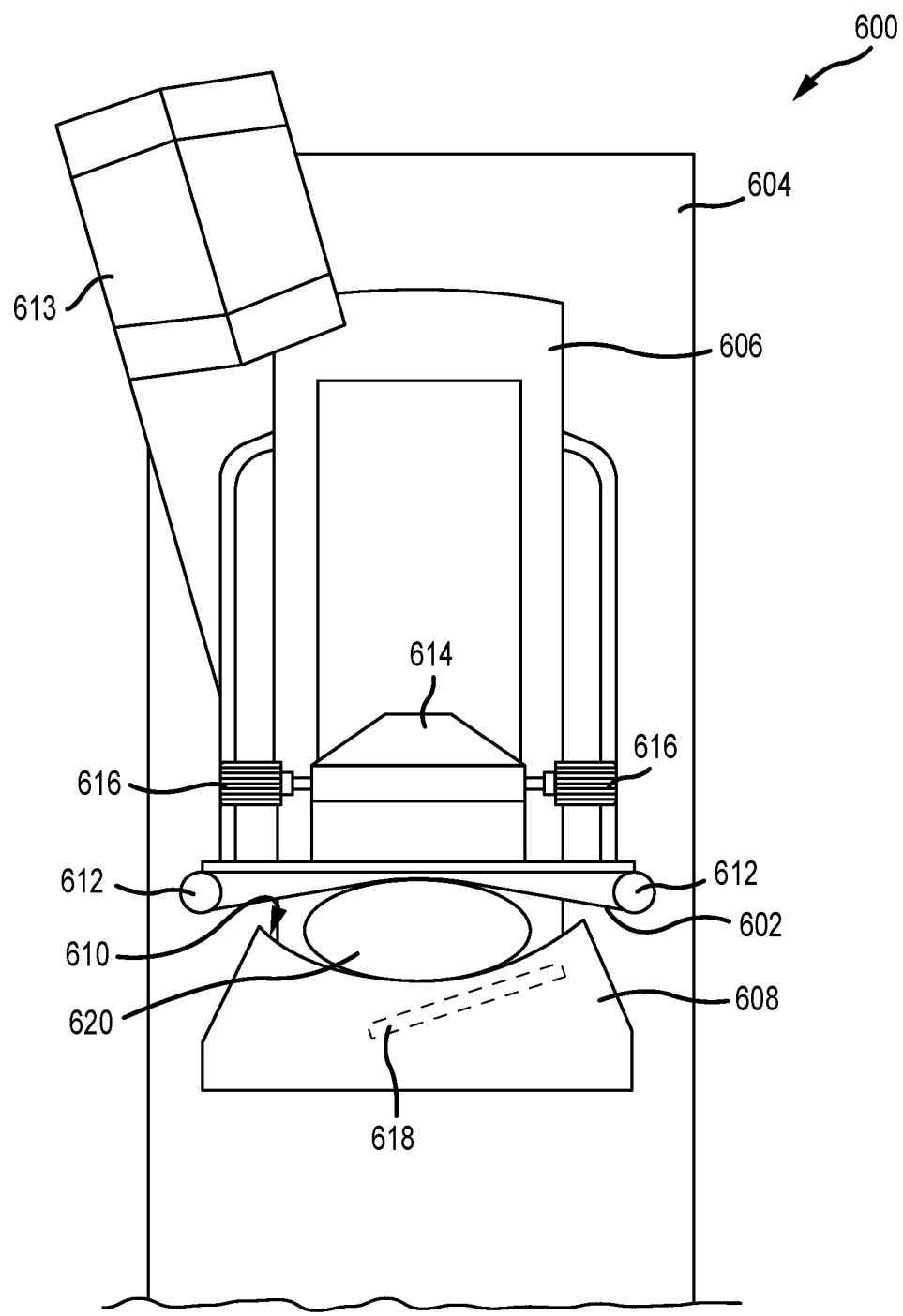

FIGS. 6A and 6B depict a partial front view of another example of an imaging system 600 utilizing a flexible compression element 602, with the flexible compression element 602 depicted in a first position and a second position, respectively. The imaging system includes a gantry 604 and a compression system 606. The compression system includes both the flexible compression element 602 and a breast support platform 608 that, in this example, has a curved support surface 610. The imaging system 600 also includes a tube head 613 that is pivotably mounted to the gantry 604. The compression system 606 is also pivotably mounted to the gantry 604. Both the tube head 613 and the compression system 606 may be pivotable about the same compression system axis A. The curved support surface 610 may have a curvature approximating that of an ellipse or other geometric structure. Since the breast support platform 608 extends away from the chest wall, it forms a generally curved concave surface for supporting a breast. The curvature may be about compression system axis A, or a different axis that is also generally parallel to the compression system axis A. An x-ray receptor 618 disposed below the curved support surface 610 may also pivot in response to pivoting of the tube head 613 during imaging procedures.

The flexible compression element 602 may include two lateral arms 612 connected to a compression arm 614, which may be actuated (raised or lowered) manually via knobs 616 or electronically by buttons or foot pedals (not shown). The flexible compression membrane 602 spans the lateral arms 612. Although only two lateral arms 612 are depicted, the compression system 606 described herein may also include a span that is disposed proximate the chest wall, such as depicted in FIGS. 3-4B.

FIG. 6B depicts the breast compression system 606 lowered so as to stabilize and compress somewhat a breast 620. The breast 620 is supported from below by the breast support platform 608 and a lower surface of the breast obtains a curvature similar to that of the curved support surface. The flexible compression membrane 602 is pressed against the breast 620, deforming while doing so, such that the breast attains a substantially oval shape. This oval shape may be sufficient for imaging of the breast, for example, in a tomosynthesis imaging procedure. The lateral arms 612 may also be able to move laterally or rotate, as described in conjunction with FIG. 2, so as to also the tension of the flexible membrane 602.

Figure 7:
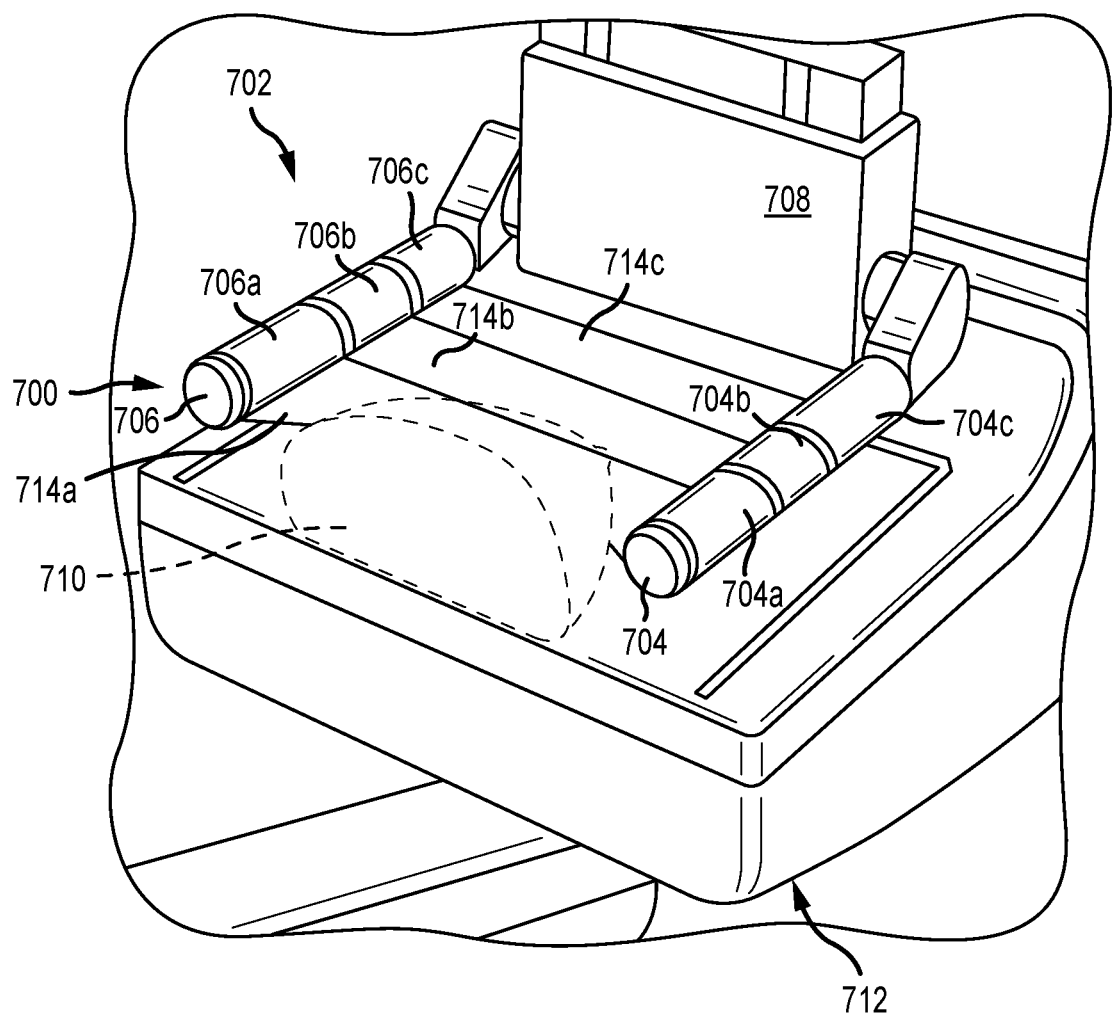
FIG. 7 depicts a partial perspective view of an imaging system utilizing another example of a flexible compression element.

FIG. 7 illustrates an imaging system 700 that includes a flexible membrane compression system 702 having a pair of opposing lateral arms 704 and 706. Each of the arms 704, 706 are attached to a base compression system 708, which may be raised and lowered as described herein so as to compress a breast 710 against a breast support platform 712. Unlike the previous examples, where a single flexible membrane spans the arms, the depicted configuration includes multiple flexible compression membranes 714*a-c*. Each of the flexible membranes 714*a-c* span a corresponding portion 704*a-c*, 706*a-c* of the two lateral arms 704, 706. In that case, each flexible membrane 714*a-c* may be individually tensioned (e.g., by a rotatable sheath on each portion 704*a-c*, 706*a-c*). This allows for individual tension control along the length of each arm 704, 706 and, accordingly, individual tension along portions of the breast 710. This configuration may aid a technician in properly positioning a breast, so as to limit folds formed in the skin or breast tissue, or over-compression of certain regions of the breast, with under-compression of other regions. For example, more compression may be desirable at the chest wall, so as to keep the patient stabilized and immobilized, while less compression may be required at the nipple end of the breast.

This disclosure described some examples of the present technology with reference to the accompanying drawings, in which only some of the possible examples were shown. Other aspects can, however, be embodied in many different forms and should not be construed as limited to the examples set forth herein. Rather, these examples were provided so that this disclosure was thorough and complete and fully conveyed the scope of the possible examples to those skilled in the art.

Although specific examples were described herein, the scope of the technology is not limited to those specific examples. One skilled in the art will recognize other examples or improvements that are within the scope of the present technology. Therefore, the specific structure, acts, or media are disclosed only as illustrative examples. Examples according to the technology may also combine elements or components of those that are disclosed in general but not expressly exemplified in combination, unless otherwise stated herein. The scope of the technology is defined by the following claims and any equivalents therein.

What is claimed is:

1. A compression element for a breast imaging system, the compression element comprising:
   a bracket body for releasably securing the compression element to a compression arm of the breast imaging system;
   a rigid frame extending from the bracket body, wherein the rigid frame comprises:
      a first lateral arm extending from the bracket body;
      a second lateral arm extending from the bracket body substantially parallel to the first lateral arm; and
      a span connecting the first lateral arm and the second lateral arm, wherein the span connects ends of the first lateral arm and the second lateral arm at a location opposite the bracket body;
   a flexible membrane extending from the span towards the bracket body; and
   a position adjustment mechanism secured to the bracket body, wherein a portion of the flexible membrane disposed opposite the span is secured to the position adjustment mechanism, and wherein the position adjustment mechanism comprises:
      a housing secured to the bracket body and elongated in a direction that is substantially orthogonal to the extension of the first and second lateral arms;
      an actuator disposed within the housing; and
      a rod engaged with the actuator, wherein the rod comprises an interior portion disposed within the housing and an exterior portion disposed outside of the housing, and wherein the flexible membrane is secured to the exterior portion, and wherein the actuator is configured to adjust a position of the rod relative to the bracket body and along the direction of the elongated housing.

2. The compression element of claim 1, wherein the flexible membrane is overmolded onto at least a portion of the span.

3. The compression element of claim 2, wherein lateral edges of the flexible membrane are not secured to the rigid frame.

4. The compression element of claim 1, wherein the bracket body comprises a pivoting bracket for releasably securing the compression element to the compression arm.

5. The compression element of claim 1, further comprising a breast support platform disposed above an x-ray receptor of the breast imaging system.

6. The compression element of claim 5, wherein the breast support platform is curved.

7. The compression element of claim 6, wherein the curved breast support platform comprises a support platform axis extending substantially orthogonal to a patient-facing surface of the support platform.

8. The compression element of claim 7, wherein the curved breast support platform is curved around the support platform axis.

9. The compression element of claim 7, wherein the curved breast support platform maintains a curvature of a lower portion of a breast during imaging.

10. The compression element of claim 9, wherein the flexible membrane maintains a curvature of an upper portion of the breast during imaging.

11. The compression element of claim 10, wherein at least one of the curvatures is about the support platform axis.

12. The compression element of claim 1, wherein the bracket body spans the first lateral arm and the second lateral arm.

13. A compression element for a breast imaging system, the compression element comprising:
   a rigid unitary frame comprising:
      a bracket body comprising a bracket connection;
      a first lateral arm extending from a first end of the bracket body;
      a second lateral arm extending from a second end of the bracket body; and
      a span extending between the first lateral arm and the second lateral arm, wherein the span comprises a profile having a substantially vertical major axis, and wherein the span is curved between the first lateral arm and the second lateral arm such that a lower edge at a mid-portion of the span is disposed above a lower edge of both the first lateral arm and the second lateral arm; and
   a flexible membrane spanning the rigid unitary frame, wherein a portion of the flexible membrane connected to the span at the mid-portion extends at least partially along the vertical major axis and the portion of the flexible membrane is configured to apply a compression force to a breast proximate a chest wall.

14. The compression element of claim 13, wherein the rigid unitary frame comprises smooth curved corners at each end of the bracket body, the first lateral arm, the second lateral arm, and the span.

15. The compression element of claim 13, wherein the flexible membrane is overmolded over at least a portion of the rigid unitary frame.

16. The compression element of claim 13, wherein the bracket connection comprises a post extending from the bracket body.

17. The compression element of claim 13, wherein the bracket connection comprises a rotatable connector.

18. The compression element of claim 17, wherein the rotatable connector is configured to couple to a compression arm, the rotatable connector defining a pivot axis that is substantially orthogonal to the compression arm such that the rigid unitary frame is pivotable around the pivot axis.

19. The compression element of claim 18, wherein the rotatable connector provides a biasing force to the rigid unitary frame towards a generally level orientation relative to horizontal.

\* \* \* \* \*